United States Patent
Minagawa et al.

(10) Patent No.: US 8,204,832 B2
(45) Date of Patent: Jun. 19, 2012

(54) MEDICAL IMAGE DIAGNOSTIC APPARATUS AND REMOTE MAINTENANCE SYSTEM

(75) Inventors: Katsuyuki Minagawa, Tokyo (JP); Etsuji Katono, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 522 days.

(21) Appl. No.: 12/445,608

(22) PCT Filed: Sep. 26, 2007

(86) PCT No.: PCT/JP2007/068701
§ 371 (c)(1),
(2), (4) Date: Apr. 15, 2009

(87) PCT Pub. No.: WO2008/050571
PCT Pub. Date: May 2, 2008

(65) Prior Publication Data
US 2010/0316266 A1    Dec. 16, 2010

(30) Foreign Application Priority Data
Oct. 27, 2006    (JP) .................... 2006-291894

(51) Int. Cl.
*G06F 21/00* (2006.01)
*G06Q 10/00* (2012.01)
*G06Q 50/00* (2012.01)

(52) U.S. Cl. ............ 705/51; 705/50; 705/2; 705/3
(58) Field of Classification Search .......... 705/2–3, 705/50–51
See application file for complete search history.

(56) References Cited

U.S. PATENT DOCUMENTS

| | | | |
|---|---|---|---|
| 6,178,225 B1 * | 1/2001 | Zur et al. ............ | 378/98.2 |
| 6,259,706 B1 * | 7/2001 | Shimada ............. | 370/466 |
| 6,925,367 B2 * | 8/2005 | Fontius .............. | 701/33 |
| 7,046,134 B2 * | 5/2006 | Hansen .............. | 340/506 |
| 7,050,984 B1 * | 5/2006 | Kerpelman et al. ... | 705/2 |
| 7,127,371 B2 * | 10/2006 | Duckert et al. ...... | 702/179 |

(Continued)

FOREIGN PATENT DOCUMENTS
JP    2003-190105    7/2003
(Continued)

OTHER PUBLICATIONS

"De-identification", UC-Davis Health Systems website, all pages, Aug. 7, 2007. http://web.archive.org/web/20070807075501/http://www.ucdmc.ucdavis.edu/compliance/guidance/privacy/deident.html.*

(Continued)

*Primary Examiner* — James A Reagan
*Assistant Examiner* — Calvin Cheung
(74) *Attorney, Agent, or Firm* — Cooper & Dunham LLP

(57) ABSTRACT

A remote maintenance system for medical image diagnostic apparatuses capable of preventing leak of personal information on the patient attached to a medical image.
The system comprises an MRI apparatus (100), a server (300) installed in a service center of a company performing the maintenance service on the MRI apparatus (100), and a network facility (200) for interconnecting the server (300) and the MRI apparatus (100).
The server (300) transmits a permission request for remote connection to the MRI apparatus (100) through the network facility (200).
If the remote connection is permitted, a VPN control unit (8a) of the MRI apparatus (100) converts the personal information on the medical image into a concealed mark and transmits it along with the medical image to the server (300).

5 Claims, 9 Drawing Sheets

U.S. PATENT DOCUMENTS

| | | | |
|---|---|---|---|
| 7,158,979 B2* | 1/2007 | Iverson et al. | 707/741 |
| 7,890,887 B1* | 2/2011 | Linardos et al. | 715/810 |
| 7,970,623 B2* | 6/2011 | Miyauchi et al. | 705/2 |
| 2002/0090142 A1* | 7/2002 | Igarashi et al. | 382/246 |
| 2002/0112733 A1* | 8/2002 | Miyauchi et al. | 128/925 |
| 2002/0188187 A1 | 12/2002 | Jordan | |
| 2002/0198997 A1* | 12/2002 | Linthicum et al. | 709/227 |
| 2003/0139665 A1* | 7/2003 | Takayama et al. | 600/407 |
| 2003/0236450 A1* | 12/2003 | Kocinski | 600/300 |
| 2004/0172302 A1* | 9/2004 | Martucci et al. | 705/2 |
| 2004/0181368 A1* | 9/2004 | Breunissen et al. | 702/184 |
| 2005/0071188 A1* | 3/2005 | Thuerk | 705/2 |
| 2005/0148849 A1* | 7/2005 | Heere et al. | 600/407 |
| 2005/0165623 A1* | 7/2005 | Landi et al. | 705/2 |
| 2005/0234330 A1* | 10/2005 | Yokoi et al. | 600/410 |
| 2005/0234740 A1* | 10/2005 | Krishnan et al. | 705/2 |
| 2005/0236474 A1* | 10/2005 | Onuma et al. | 235/382 |
| 2006/0155578 A1* | 7/2006 | Eisenberger et al. | 705/2 |
| 2006/0266826 A1* | 11/2006 | Banfield et al. | 235/383 |
| 2007/0065033 A1* | 3/2007 | Hernandez et al. | 382/239 |
| 2007/0168223 A1* | 7/2007 | Fors et al. | 705/2 |
| 2007/0255704 A1* | 11/2007 | Baek et al. | 707/6 |
| 2008/0004506 A1* | 1/2008 | Ikeda et al. | 600/300 |
| 2008/0185425 A1* | 8/2008 | Roberts et al. | 235/375 |

FOREIGN PATENT DOCUMENTS

| | | |
|---|---|---|
| JP | 2005-184731 | 7/2005 |
| JP | 2005-296333 | 10/2005 |
| JP | 2006-343944 | 12/2006 |
| JP | 2007-207181 | 8/2007 |
| WO | WO02/100090 A1 | 12/2002 |

OTHER PUBLICATIONS

"Overview of the HIPAA Final Privacy Regulations", Partners Healthcare System website, all pages, Mar. 20, 2005. http://web.archive.org/web/20050320130918/http://healthcare.partners.org/phsirb/hipaaov.htm.*

* cited by examiner

FIG.8

| NAME | CONCEALED INFORMAITON | FLAG |
|---|---|---|
| TARO HITACHI | *** | 1 |
| HANAKO HITACHI | *** | 0 |

801 — NAME
802 — CONCEALED INFORMAITON
803 — FLAG
800

MEDICAL IMAGE DIAGNOSTIC APPARATUS AND REMOTE MAINTENANCE SYSTEM

TECHNICAL FIELD

The present invention relates to a medical image diagnostic apparatus and a remote maintenance system for medical image diagnostic apparatuses including a magnetic resonance imaging (hereinafter referred to as "MRI") apparatus.

BACKGROUND ART

A remote maintenance system for medical image diagnostic apparatuses is provided with a medical image diagnostic apparatus to be installed in a facility at which a user works such as hospitals, a server installed in a service center of a company performing maintenance service on the medical image diagnostic apparatus, and a network facility for interconnecting the medical image diagnostic apparatus and the server.

In the remote maintenance system of the medical image diagnostic apparatus, the service wherein the server deals with the troubles of medical imaging, etc. using the medical imaging diagnostic apparatus is carried out online. An operation example thereof is identifying problems of a medical image diagnostic apparatus using medical images imaged at a facility such as a hospital, as disclosed in Patent Document 1.

Patent Document 1: JP-A-2003-190105

However, there does not appear to be a concern in Patent Document 1 with respect to protecting personal information of medical images to he used for finding problems in medical image diagnostic apparatuses. Thus the unsolved problem of the need to prevent leaking of personal information on patients attached to the medical images still remains.

BRIEF SUMMARY

In an aspect of this disclosure, there are provided a medical image diagnostic apparatus and a remote maintenance system for the medical image diagnostic apparatus, that are capable of preventing leakage of personal information on patients attached to the medical images.

In another aspect, the medical image diagnostic apparatus is configured as below.

The medical image diagnostic apparatus has:

imaging means for performing imaging of an object to be examined; and display means for displaying the image of the object, characterized in further comprising:

personal information input means for inputting personal information on the object;

storage means for storing the personal information inputted by the personal information input means and an image of the object imaged by the imaging means; and conversion processing means connected to a communication network, for converting the personal information of the object stored in the storage means into a concealed mark in response to the request to send image data received via the communication network, and transmitting the image of the object to the communication network along with the converted concealed mark.

Also, the aforementioned remote maintenance system of the medical image diagnostic apparatus is configured as below.

The remote maintenance system of the medical image diagnostic apparatus has:

a medical image diagnostic apparatus;

a server installed in a service center of a company performing the maintenance of the medical image diagnostic apparatus; and a communication network for interconnecting the server and the medical image diagnostic apparatus, wherein:

the server comprises image display means, and a display control unit for transmitting request for remote connection to the medical image diagnostic apparatus via the communication network and displays the image transmitted from the medical image diagnostic apparatus on the image display means via the communication network; and the medical image diagnostic apparatus comprises conversion processing means for converting personal information of the object into a concealed mark in response to the request for remote communication transmitted from the server and transmitting an image of the object along with the converted concealed mark to the communication network.

In accordance with the aforementioned medical image diagnostic apparatus, personal information attached to medical images can be concealed, and leaking of personal information on patients can be prevented.

BRIEF DESCRIPTION OF THE DIAGRAMS

FIG. 8 is chart illustrating an example of storage content in the common conversion table of FIG. 7 and FIG. 9.

DESCRIPTION OF REFERENCE NUMERALS

2: static magnetic field generating system, 3: gradient magnetic field generating system, 4: sequencer, 5: transmitting system, 6: receiving system, 7: signal processing system, 8: CPU, 8*a*: VPN control unit, 18: magnetic disk, 19: optical disk, 20: display, 21: ROM, 22: RAM, 25: operation unit, 100: MRI apparatus, 200: network facility, 300: server, 301: display control unit, 302: display device

BEST MODE FOR CARRYING OUT THE INVENTION

Hereinafter, preferable embodiments of the medical image diagnostic apparatus and the remote maintenance system for medical image diagnostic apparatuses of the present invention will be described in detail referring to the attached diagrams. In all of the diagrams for illustrating embodiments of the invention, the places having the same function are appended with the same symbols, and the repeated explanation thereof will be omitted.

First, a general outline of an MRI apparatus will be explained based on FIG. 1 as an example to which the medical image diagnostic apparatus related to the present invention is applied.

Figure 1:
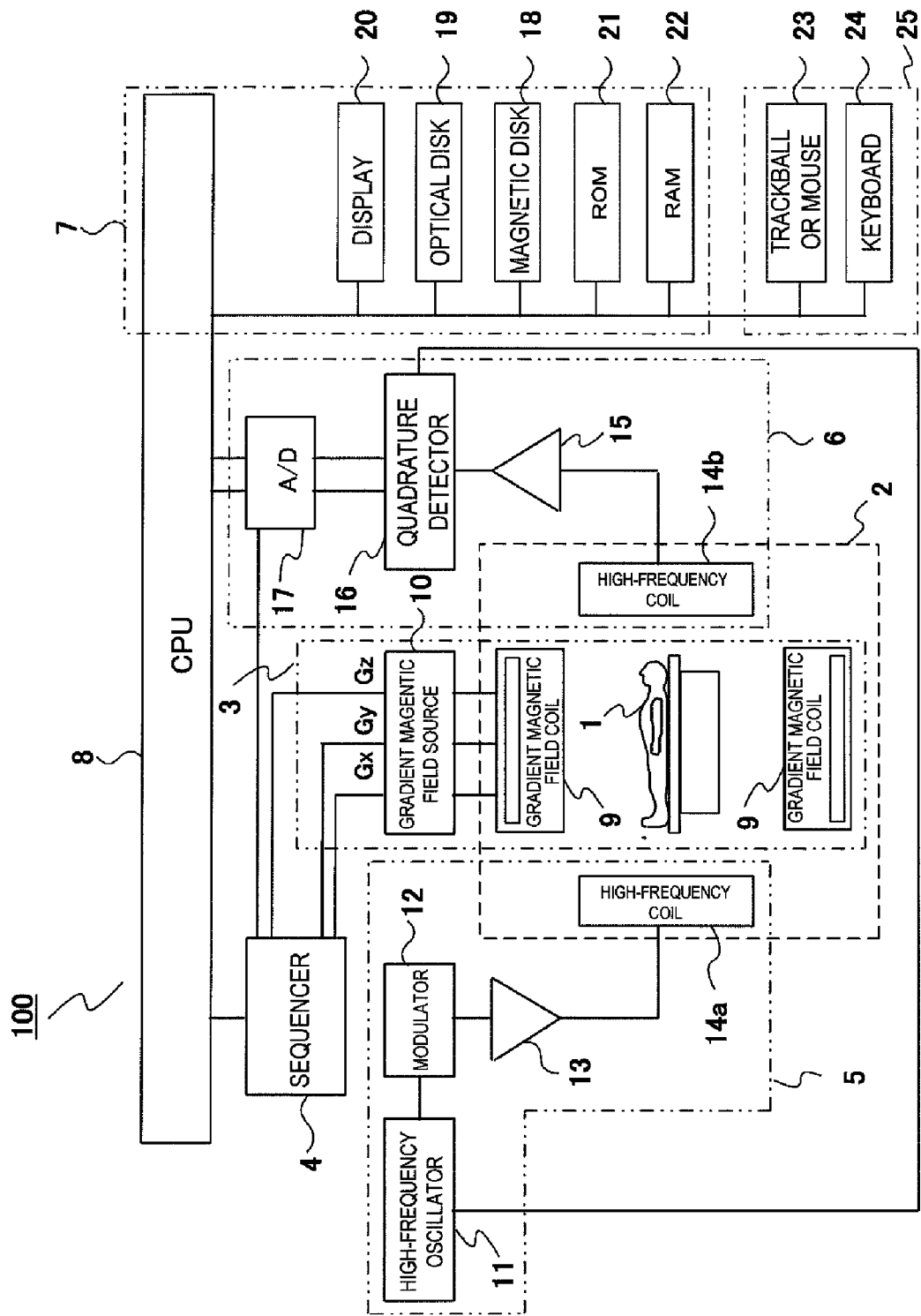
FIG. 1 is a block diagram showing the general configuration in an example of a MRI apparatus to which the present invention is applied.

FIG. 1 is a block diagram showing a general configuration of an example of the MRI apparatus to which the present invention is applied. This MRI apparatus is for acquiring a tomographic image of an object to be examined using nuclear magnetic resonance phenomenon, comprising static magnetic field generating system 2, gradient magnetic field generating system 3, transmitting system 5, receiving system 6, signal processing system 7, sequencer 4 and central processing unit (CPU) 8 by which imaging means is formed, as shown in FIG. 1.

The static magnetic field generating system 2 is for generating a uniform static magnetic field, either in the direction orthogonal to the body axis in the space around the object 1 if it is the vertical magnetic field method type or in the body-axis direction if it is the horizontal magnetic field type, wherein a static magnetic field generating source of permanent magnetic method, normal conducting method or superconducting method is placed around the object 1.

The gradient magnetic field generating system 3 is formed by a gradient magnetic field coil 9 coiled in 3 axis-directions of X, Y and Z which are the coordinate system (coordinate system rest) of the MRI apparatus and a gradient magnetic field source 10 for driving the respective gradient magnetic field coils, for applying gradient magnetic fields Gx, Gy and Gz in the 3 axis-directions of X, Y and Z by driving the gradient magnetic field source 10 of the respective coils in accordance with the command from the sequencer 4 to be described later.

Upon imaging, the sliced plane with respect to the object 1 is set by applying a slice direction gradient magnetic field pulse (Gs) in the direction orthogonal to the slice plane (imaged cross-section), a phase encode direction gradient magnetic field pulse (Gp) and a frequency encode direction gradient magnetic field pulse (Gf) are applied in the remaining two directions which are orthogonal to the slice plane and to each other, and positional information of the respective directions are encoded to the echo signals.

The sequencer 4 is control means for repeatedly applying a high-frequency magnetic pulse (hereinafter referred to as "RF pulse") and a gradient magnetic field pulse in a predetermined pulse sequence, being operated under the command of the CPU 8, and transmits various sorts of commands necessary for collecting data for a tomographic image of the object 1 to the transmitting system 5, the gradient magnetic field generating system 3 and the receiving system 6.

The transmitting system 5 is for irradiating RF pulses to the object 1 for generating nuclear magnetic resonance to atomic nuclear spin by which the biological tissues of the object 1 are composed, comprising a high-frequency oscillator 11, modulator 12, high-frequency amplifier 13 and high-frequency coil (transmission coil) 14a on the transmitting side. The RF pulses are irradiated to the object 1 by performing amplitude modulation by the modulator 12 on the high-frequency pulses outputted from the high-frequency oscillator 11 in the timing by the command issued from the sequencer 4 and providing the amplitude-modulated high-frequency pulses to the high-frequency coil 14a placed in the vicinity of the object 1 after being amplified by the high-frequency amplifier 13.

The receiving system 6 is for detecting the echo signals (NMR signals) emitted by nuclear magnetic resonance of nuclear spin by which biological tissues of the object 1 are composed, formed by a high-frequency coil (receiving coil) 14b on the receiving side, signal amplifier 15, quadrature detector 16 and A/D converter 17. The responsive NMR signals of the object 1 induced by electromagnetic waves irradiated from the high-frequency coil 14a on the transmitting side are detected by the high-frequency coil 14b placed in the vicinity of the object 1, amplified by the signal amplifier 15, divided into orthogonal diphyletic signals by quadrature detector 16 in a timing by the command issued from the sequencer 6, each of the divided signals are converted into digital quantity in the A/D converter 17 and transmitted to the signal processing system 7.

The signal processing system 7 is for processing various data to display and storing the processed data, comprising external storage device such as optic disk 19, magnetic disk 18, etc. and a display 20 formed by CRT, etc. Upon input of data from the receiving system 6 to the CPU 8, the CPU 8 performs processing such as signal processing and image reconstruction, displays the result of the processing that are tomographic images of the object 1 to a display 20, and saves them to the external storage device such as the magnetic disk 18.

The operation unit (personal information input means) 25 is for inputting various control information of the MRI apparatus, control information of the processing to be performed in the signal processing system 7, or personal information such as the name of the individual of the image, formed by a trackball or a mouse 23 and a keyboard 24. This operation unit 25 is placed in the vicinity of the display 20, and an operator controls various processing of the MRI apparatus interactively through the operation unit 25 while observing the display 20.

The high-frequency coil 14a and the gradient magnetic field coil 9 are disposed in the static magnetic field space of the static magnetic field generating system 2 into which the object 1 is placed, either with respect to the object 1 if it is the vertical magnetic field type or surrounding the object 1 if it is the horizontal magnetic field type. Also, high-frequency coil 14b on the receiving side is disposed either with respect to the object 1 or surrounding the object 1.

Currently, imaging target nuclide of MRI apparatuses which is common in clinical practice is hydrogen coleus (proton) which is the main component of the object. By imaging information in relation to spatial distribution of proton density or spatial distribution of relaxation time in the exited state, forms or functions of body parts such as head, abdomen and extremities are imaged two-dimensionally or three-dimensionally.

Figure 2:
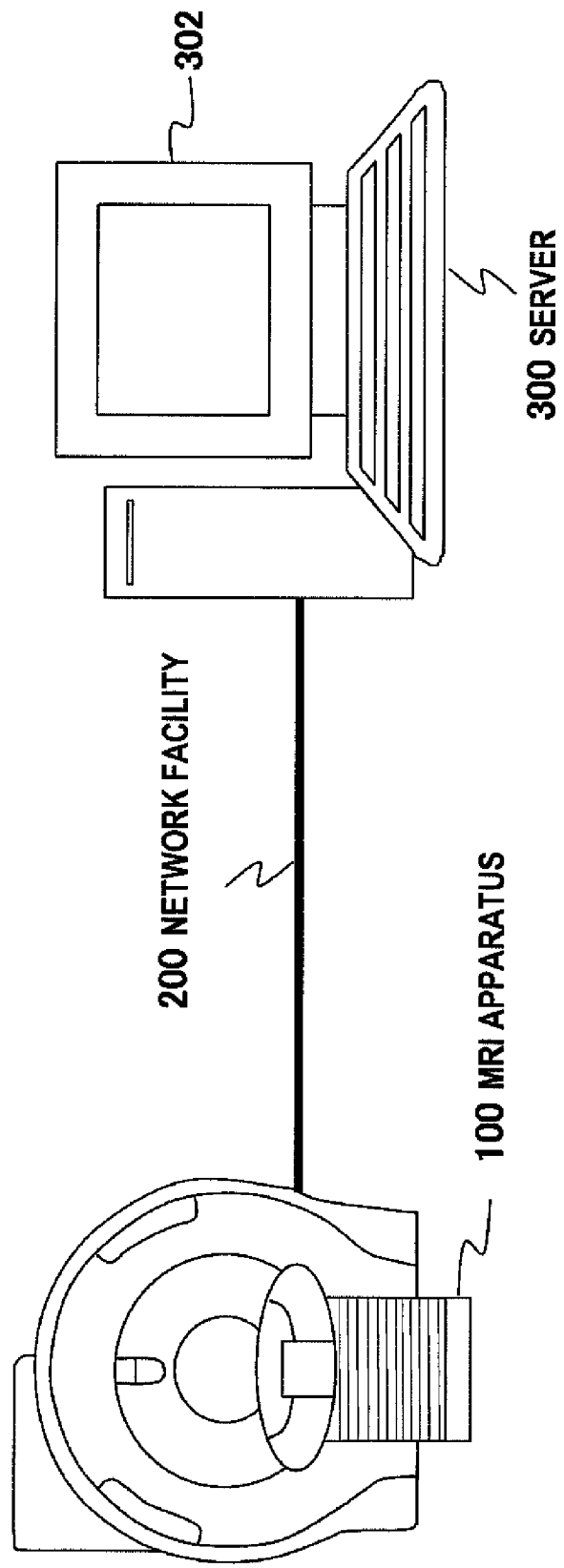
FIG. 2 is a schematic configuration diagram of a remote maintenance system of the MRI apparatus to which the present invention is applied.

In the above-described MRI apparatus 100, a server is connected via the communication network facility, and the remote maintenance system of the MRI apparatus is configured as shown in FIG. 2.

Figure 3:
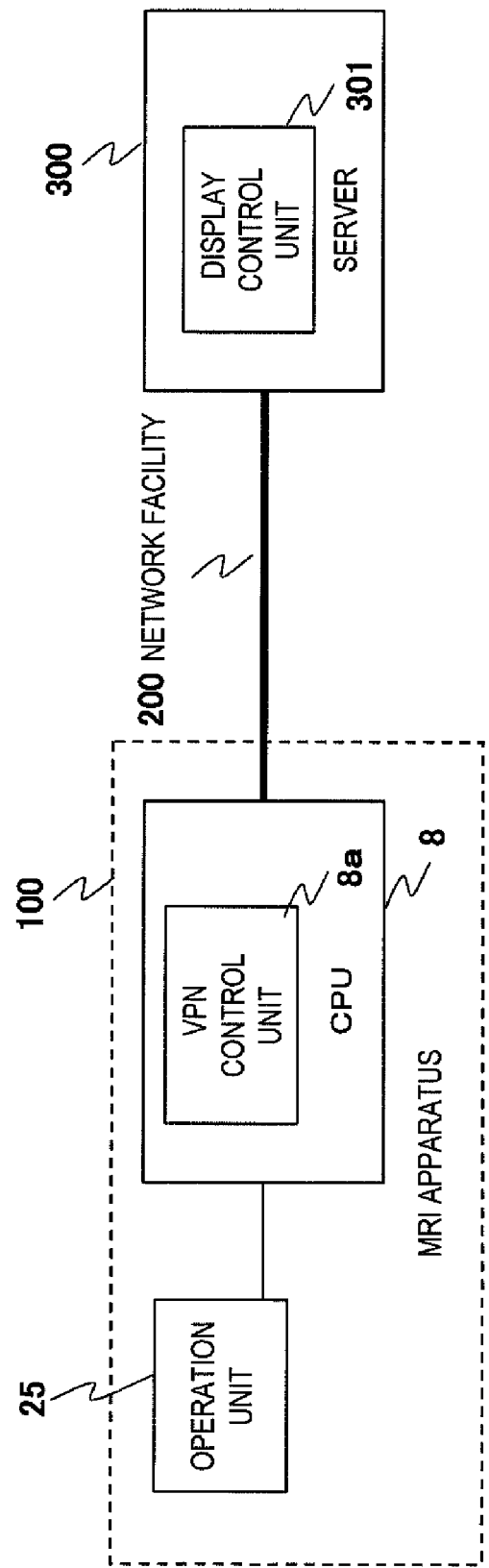
FIG. 3 is a block diagram illustrating the function of FIG. 2.

FIG. 2 is a schematic configuration diagram of the remote maintenance system of the MRI apparatus related to the present invention, and FIG. 3 is a block diagram illustrating the function of FIG. 2.

The remote maintenance system of the MRI apparatus has the MRI apparatus 100, a server 300 and a communication network facility 200 to connect the apparatus and the server as shown in FIG. 2.

The explanation of the MRI apparatus will be omitted to avoid repetition.

The server 300 comprising a display device 302, etc. is installed in a service center of a company to perform maintenance service on the MRI apparatus 100, and is mutually connected via the MRI apparatus 100 and the network facility 200 so that remote-operation can be performed among them.

The remote maintenance system of the MRI apparatus is shown as FIG. 3 when integrated by its function. In FIG. 3, the MRI apparatus 100 has an operation unit 25 and the CPU 8 to be connected capable of signal transmission/reception to/from the server 300, wherein the data controlled by the CPU 8 is outputted to the network facility 200. The CPU 8 further comprises a Virtual Private Network (hereinafter referred to as the VPN) management unit (conversion processing means) 8a.

When the server 300 is connected and in communication with the MRI apparatus 100 using function of remote desktop, the VPN control unit 8a recognizes it as an event of connection. The operator on the MRI apparatus 100 side sets in advance personal information for identifying an individual such as the name, gender, weight, birth date, hospital name, examination date and time, patient ID, social insurance number referred to as social security number in the United States, Basic Residential Registers number in Japan and driver's license number, using the operation unit 25. The set personal information of the patient is stored in a memory (magnetic disk 18, optical disk 19 or RAM 22, etc.) along with the image information of the patient.

The VPN is an encrypted transmission technique without depending on application software, and is a technique which has been sequentially replaced with conventional SSL (Secure Sockets Layer) for providing cryptographic connection on a Web base or a cryptography method of e-mail.

The VPN control unit 8a performs processing to conceal the set personal information. The server 300 has a display control unit 301, and displays the MRI image wherein the personal information is concealed by the VPN control unit 8a on the display device 302. Also, VPN control unit 8a is capable of storing the MRI image wherein the personal information is concealed to the optical disk 19, magnetic disk 18 or the RAM 22.

While the approximate configuration of the present invention is as described above, the operation thereof is different in each embodiment. The respective embodiments of the present invention will be described below.

[First Embodiment]

The first embodiment of the present invention will be described using FIG. 4 and FIG. 5.

Figure 4:
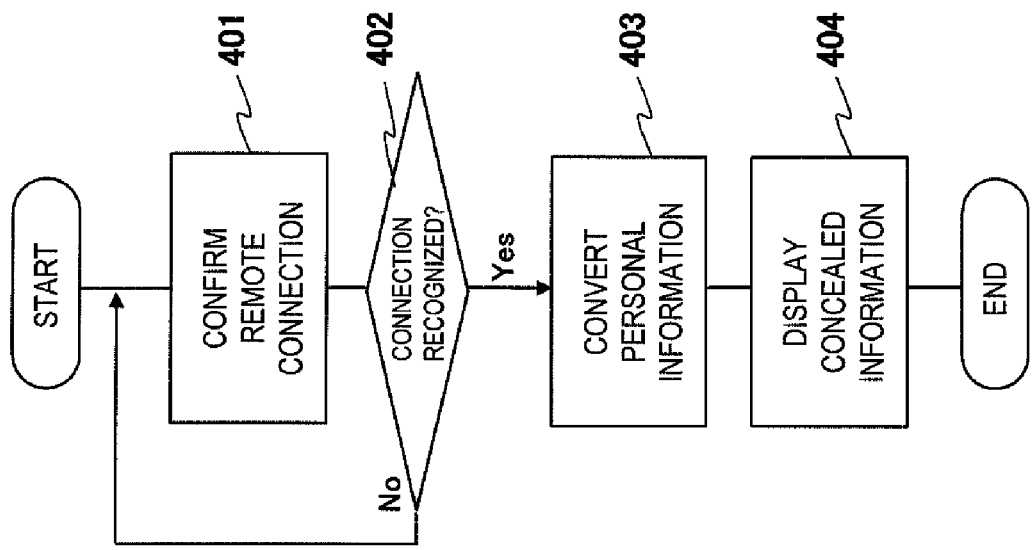
FIG. 4 is a flowchart illustrating the operation of an embodiment 1 of the present invention.
Figure 5:
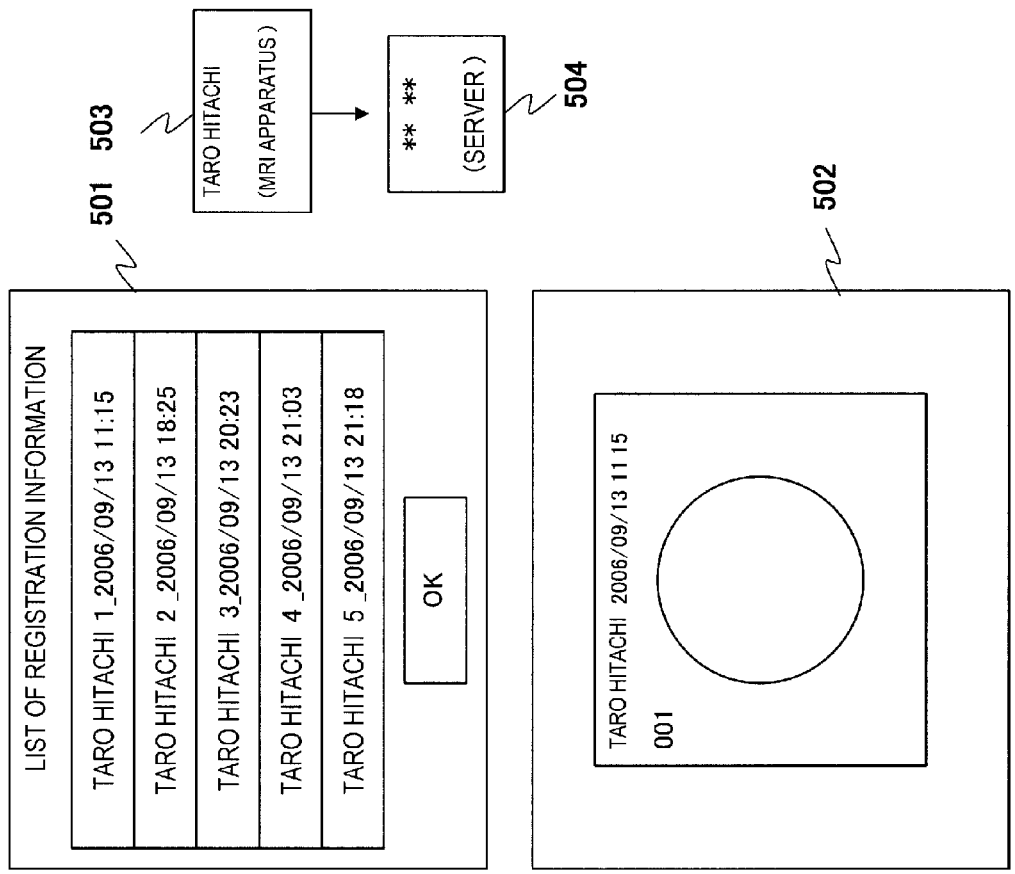
FIG. 5 shows a display example for illustrating the operation procedure of FIG. 4.

FIG. 4 is a flowchart illustrating the operation of the first embodiment related to the present invention, and FIG. 5 is a display example for illustrating the operation procedure of FIG. 4.

In FIG. 4 and FIG. 5, the server 300 performs the confirmation of remote-connection on the MRI apparatus 100 (step 401). Prior to the operation, the user of the MRI apparatus 100 sets the mode which is "connection recognized" or "connection not recognized" in the mode storage region so that the server 300 can recognize the mode of the CPU 8 in the MRI apparatus 100 via the network facility 200.

The server 300 intercommunicates with the MRI apparatus 100 via the network facility 200. In accordance with the mode set in the mode storage region, if the mode is "connection recognized" (recognition of transmission) a step 403 is carried out, and if the mode is "connection not recognized" (nonrecognition of transmission) the operation stays in a standby state (step 402).

The VPN control unit 8a of the MRI apparatus 100 performs concealing process on a patient's name as shown in FIG. 5. In concrete terms, an individual name of a patient such as "Taro Hitachi" 503 is converted into a concealed mark " " 504 (step 403). The concealing target is not only a patient list 501 and an MRI image 502 but all of the displayed personal information.

The display control unit 301 of the server 300 displays the concealed personal information and the image from the MRI apparatus 100 on the display device 302 (step 404).

Then on the server 300 side, problems, etc. of the medical image diagnostic apparatus are determined by analysis of the image displayed on the display device 302.

As described above, in accordance of the embodiment 1 related to the present invention, upon determining the problems, etc. of the medical image diagnostic apparatus using a medical image on the server 300, leaking of personal information of patients can be prevented since personal information attached to the medical image is performed with concealing process on the MRI apparatus side.

[Second Embodiment]

Next, the second embodiment of the present invention will be described referring to FIG. 6.

Figure 6:
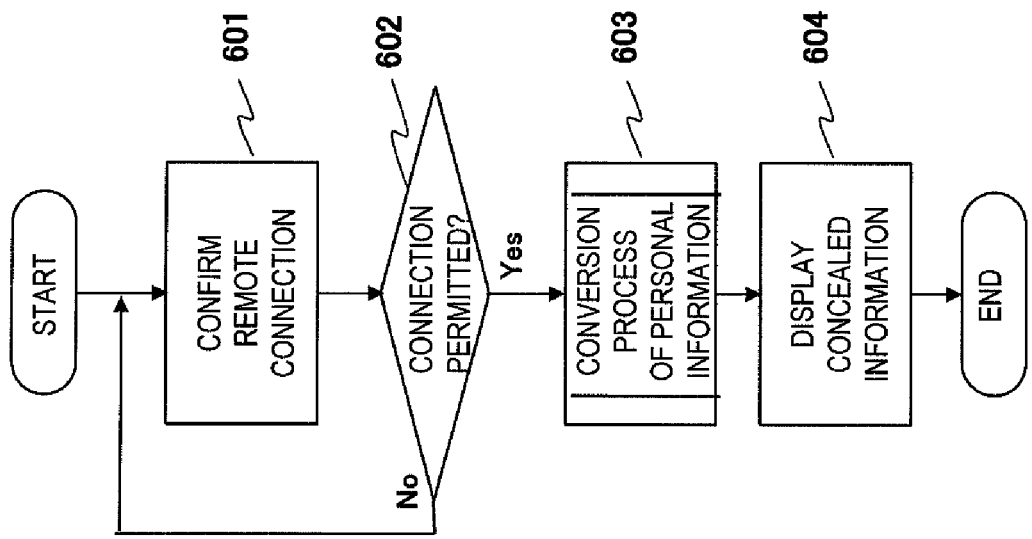
FIG. 6 is a flowchart illustrating the common operation of second and third embodiments related to the present invention.

FIG. 6 is a flowchart illustrating the operation of the second and third embodiments of the present invention.

In FIG. 6, the server 300 remotely performs the connection confirmation on the MRI apparatus 100 (step 601).

When the mode is "connection recognized" the server 300 carries out step 603, and when the mode is "connection not recognized" the process returns to step 601 and stands by until the connection is recognized (step 602).

Figure 9:
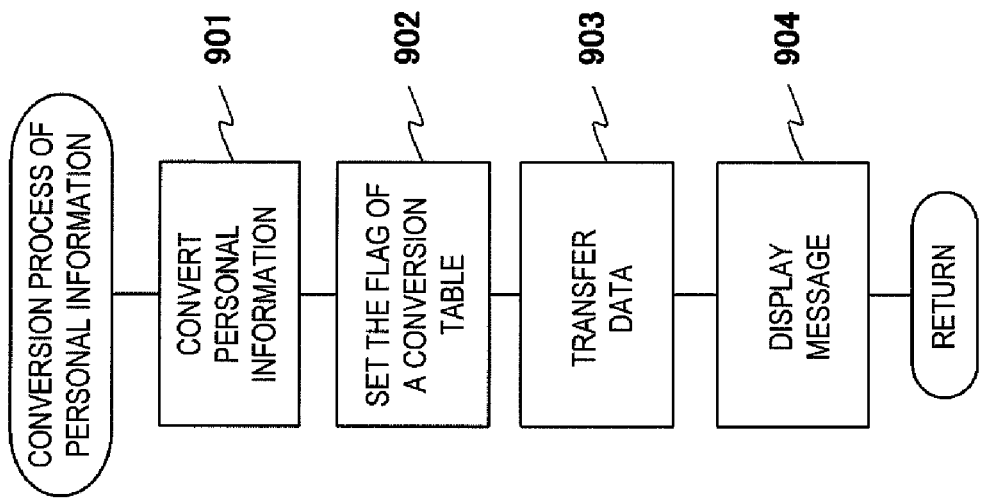
FIG. 9 is a flowchart showing the subroutine illustrating the operation of the third embodiment in FIG. 6.

Conversion of personal information is processed differently depending on the second embodiment (FIG. 7) or the third embodiment (FIG. 9).

The VPN control unit 8a of the MRI apparatus 100 performs the concealing process on the patient's name as shown in FIG. 5 (step 603).

The display control unit 301 of the server 300 displays the concealed mark of the personal information concealed by the VPN control unit 8a of the MRI apparatus 100 and the image from the MRI apparatus 100 to the display device 302 (step 604).

Figure 7:
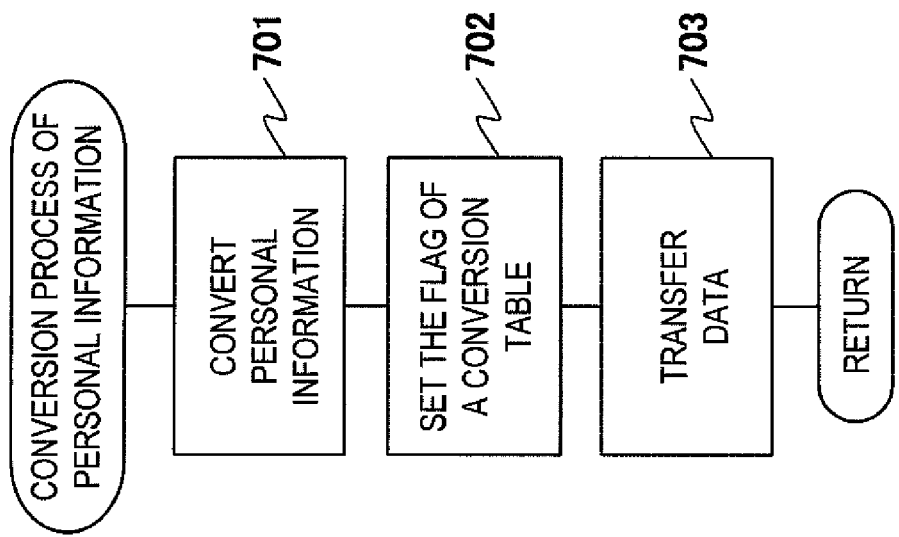
FIG. 7 is a flowchart showing the subroutine illustrating the operation of the second embodiment in FIG. 6.

FIG. 7 is a flowchart showing the subroutine of FIG. 6, showing the operation of the second embodiment. Also, FIG. 8 is an example of the storage content of the common conversion table in FIG. 7 and FIG. 9.

Conversion process of personal information in the second embodiment will be described using FIG. 7.

The VPN control unit 8a of the MRI apparatus 100 performs concealing process on the patient's name and replaces it with the concealed mark as shown in FIG. 5 (step 701).

The VPN maintenance unit 8a of the MRI apparatus 100 sets "1" on a flag 803 of a conversion table 800 after performing conversion process on the patient's name "Taro Hitachi" into the concealed mark " " as shown in FIG. 8. The conversion from the patient's name "Hanako Hitachi" to the concealed mark shown in FIG. 8 is in mid-course. Thus "** YY", not the concealed mark, is displayed and the flag is still remained as "0" (step 702).

The MRI apparatus 100 transmits the image information wherein the flag 300 of the conversion table 800 is set as 1 and the personal information is securely concealed to the server 300 (step 703).

The content of the conversion table 800 shown in FIG. 8 can he displayed on the display 20 of the MRI apparatus 100. Therefore, the user (operator, patient. etc.) can confirm that the personal information is not leaked by confirming the content or the conversion table 800.

As described above, in accordance with the second embodiment, in addition to the same effect as the first embodiment, the user can confirm that the personal information of the patient is not leaked upon receiving the remote maintenance from the service center.

[Third Embodiment]

Next, the third embodiment will be described referring to FIG. 6 and FIG. 9.

The explanation on the flowchart shown in FIG. 6 will be omitted here since it is already described above.

FIG. 9 is a flowchart illustrating the operation of the third embodiment, and the subroutine of the flowchart shown in FIG. 6.

Conversion process of personal information in the third embodiment of the present invention will be described using FIG. 9.

The explanation on steps 901~903 shown in FIG. 9 will be omitted since they are the same as steps 701~703 shown in FIG. 7.

The server 300 displays the message indicating that the personal information on the image received from the MRI apparatus 100 is surely concealed, on the display device 302 of the server 300 and the display 20 of the MRI apparatus 100 (step 904).

This message can be, for example, the comment saying "the image wherein the personal information is concealed is transmitted", or the image on which the concealed mark is displayed along with the reception date, reception number, etc. of the image from the MRI apparatus 100 may be displayed.

As described above, in accordance with the third embodiment, in addition to the same effect of the first embodiment, a company can provide assurance to the customers that the personal information of the patient is not leaked upon receiving the remote maintenance from them.

In the above-described first third embodiments, in the case that the personal information such as the name or ID of patients is concealed, in order to prevent the problem that the patient can not be identified on the MRI apparatus side when the image of the patient stored in the RAM 22 etc., needs to be selected, it is possible to display the updated Study Date or Study ID of the patient. In other words, even if the name or ID of the patient are concealed, the updated Study Date or Study ID of the patient can be displayed.

Therefore, for the examiner of the MRI apparatus 100, it is possible to easily identify the image of the patient by matching the imaged date of the patient, Study ID and the patient's ID.

By displaying the updated Study Date or Study ID of the patient along with the image thereof, the user can prevent the mix-up which can be caused by replacing the personal information of the patient with the concealed mark, when the MRI apparatus is remote-connected to the server 300.

Also, while the patient's information is replaced with the concealed mark upon remote-connection from the server 300, when the remote-connection from the server 300 is ended and the image information communication is not permitted between the server 300 and the MRI apparatus 100 any more, the concealed personal information may be returned to the unconcealed information to be displayed.

By such configuration, though personal information cannot be displayed on the display screen while the apparatus and the server 300 are interconnected, since the information can be returned to the unconcealed display immediately upon remote-connection is disconnected, it is possible to provide a sense of security to a user during performance of remote-connection.

While an MRI apparatus is cited as an example of the medical image diagnostic apparatus in the above-described embodiments of the present invention, not only the MRI apparatus but apparatuses for acquiring medical images such as X-ray imaging apparatus, X-ray CT apparatus, ultrasonic image diagnostic apparatus and nuclear medical apparatus can be applied to the present invention.

The invention claimed is:

1. A remote maintenance system of a medical image diagnostic apparatus, said remote maintenance system comprising:
    a medical image diagnostic apparatus that is configured to acquire a medical image of an object;
    a server installed in a service center of a company and disposed to perform maintenance service on the medical image diagnostic apparatus through a communication network that connects the server and the medical image diagnostic apparatus,
    wherein:
        the server includes image display means and communicates a request for authorizing telecommunication to the medical image diagnostic apparatus via the image display means and the communication network, and
        the server further comprises display control unit for causing, the medical image received from the medical image diagnostic apparatus via the communication network to be displayed by the image display means; and
        the medical image diagnostic apparatus comprises a conversion processing means for converting a part of personal information of the object into a concealed mark in response to the request for telecommunication transmitted from the server and transmits the medical image of the object along with the converted concealed mark, to the server via the communication network, and
        the medical image diagnostic apparatus further comprises image identifying means to identify the medical image of the object by reference to one or more other parts of the personal information of the object, and
        the medical image diagnostic apparatus comprises apparatus-side image display means, and displays on the apparatus-side image display means a message that the personal information of the object is converted into a concealed mark and the converted concealed mark is transmitted to the communication network along with the medical image of the object.

2. The remote maintenance system of the medical image diagnostic apparatus according to claim 1, wherein the server displays a message on the image display means of the server indicating that the concealed mark is transmitted from the medical image diagnostic apparatus via the communication network along with the medical image and the personal information is concealed.

3. The remote maintenance system according to claim 1, wherein the part of the personal information of the object includes identification of patient, and said one or more other parts of the personal information identifies the medical image without specifically identifying the patient.

4. The remote maintenance system according to claim 1, wherein the part of the personal information of the object includes identification of patient, and said one or more other parts of the personal information includes (i) date of study in which the medical image was acquired and (ii) identification of the study.

5. The remote maintenance system according to claim 1, wherein
    the medical image diagnostic apparatus comprises apparatus-side image display means that is configured to display the medical image and the personal information of the object, wherein the image display means of the server includes a remote desktop application, and the remote desktop application, when executed by the server while the medical age and the personal information of the object are displayed on the apparatus-side image display means of the medical image diagnostic apparatus, causes the medical image displayed on the apparatus-side image display means to be displayed also on the image display means of the server while the conversion processing means of the medical image diagnostic apparatus recognizes the remote desktop application in execution by the server and causes the concealed mark to be displayed, in place of part of the personal information of the object, on the image display means of the server.

* * * * *